United States Patent
Okkels (10) Patent No.: US 9,557,258 B2
(45) Date of Patent: Jan. 31, 2017

(54) FLUID COMPOSITION ANALYSIS DEVICE AND METHOD

(71) Applicant: Danmarks Tekniske Universitet, Kgs. Lyngby (DK)

(72) Inventor: Fridolin Okkels, Copenhagen Ø (DK)

(73) Assignee: Danmarks Tekniske Universitet, Kgs. Lyngby (DK)

( * ) Notice: Subject to any disclaimer, the term of this patent is extended or adjusted under 35 U.S.C. 154(b) by 0 days.

(21) Appl. No.: 14/651,173

(22) PCT Filed: Dec. 19, 2013

(86) PCT No.: PCT/DK2013/050447
§ 371 (c)(1),
(2) Date: Jun. 10, 2015

(87) PCT Pub. No.: WO2014/094791
PCT Pub. Date: Jun. 26, 2014

(65) Prior Publication Data
US 2015/0323440 A1   Nov. 12, 2015

(30) Foreign Application Priority Data
Dec. 20, 2012 (EP) .................................... 12198606

(51) Int. Cl.
*G01F 1/00* (2006.01)
*G01F 1/86* (2006.01)
(Continued)

(52) U.S. Cl.
CPC ......... *G01N 11/04* (2013.01); *B01L 3/502746* (2013.01); *G01N 11/08* (2013.01);
(Continued)

(58) Field of Classification Search
None
See application file for complete search history.

(56) References Cited

U.S. PATENT DOCUMENTS 3,138,950 A   6/1964 Welty et al.
3,952,576 A   4/1976 Drzewiecki et al.
(Continued)

FOREIGN PATENT DOCUMENTS

WO   WO 91/15750 A1   10/1991
WO   WO 2005/086883 A2   9/2005
(Continued)

OTHER PUBLICATIONS

Bandley, Helen L. et al., "Blood rheological characterization using the thickness-shear mode resonator" Biosensors and Bioelectronics, 2004, pp. 1657-1665, vol. 19.
(Continued)

*Primary Examiner* — Peter MacChiarolo
*Assistant Examiner* — Jermaine Jenkins
(74) *Attorney, Agent, or Firm* — Knobbe Martens Olson & Bear LLP (57) ABSTRACT

The invention relates in particular to a device for determining one or more fluid properties of a fluid. The device preferably comprises a flow distributor comprising a cavity, an inlet to the cavity, one or more outlets from the cavity, and one or more flow deflecting elements present in the cavity and/or one or more flow dividing wall elements of the cavity, wherein the one or more flow deflecting elements and/or the flow dividing wall elements being arranged in such a manner that it provides sub-streams of different strength through the outlet. Furthermore, the device comprises an analyzer downstream of the outlet of the flow distributor comprising means adapted to provide a read-out indicative of the strengths of sub-streams.

17 Claims, 8 Drawing Sheets

(51) Int. Cl.
*G01F 15/02* (2006.01)
*G01F 1/78* (2006.01)
*G01F 1/80* (2006.01)
*G01N 11/04* (2006.01)
*G01N 11/08* (2006.01)
*B01L 3/00* (2006.01)

(52) U.S. Cl.
CPC ............... *B01L 2300/0816* (2013.01); *B01L 2300/0864* (2013.01); *B01L 2300/0883* (2013.01); *B01L 2400/086* (2013.01)

(56) References Cited

U.S. PATENT DOCUMENTS

| | | | | |
|---|---|---|---|---|
| 4,894,146 | A * | 1/1990 | Giddings | B01D 43/00 |
| | | | | 209/12.2 |
| 4,905,503 | A | 3/1990 | Langrick et al. | |
| 5,039,426 | A * | 8/1991 | Giddings | B01D 21/00 |
| | | | | 209/127.1 |
| 6,880,576 | B2 * | 4/2005 | Karp | B01F 5/0471 |
| | | | | 137/806 |
| 7,028,536 | B2 * | 4/2006 | Karp | B01L 3/502715 |
| | | | | 73/61.52 |
| 2003/0182991 | A1 | 10/2003 | Spaid et al. | |
| 2004/0000519 | A1 * | 1/2004 | Jiang | G01N 30/0005 |
| | | | | 210/634 |
| 2009/0038379 | A1 | 2/2009 | Colin et al. | |
| 2009/0090172 | A1 | 4/2009 | Angelescu et al. | |
| 2014/0352453 | A1 * | 12/2014 | Sonnenberg | G01F 1/662 |
| | | | | 73/861.27 |

FOREIGN PATENT DOCUMENTS

| | | |
|---|---|---|
| WO | WO 2009/045677 A1 | 4/2009 |
| WO | WO 2009/061943 A9 | 5/2009 |
| WO | WO 2012/175093 A1 | 12/2012 |

OTHER PUBLICATIONS

Groisman, Alex et al., "A Microfluidic Rectifier: Anisotropic Flow Resistance at Low Reynolds Numbers" Physical Review Letters, Mar. 5, 2004, pp. 094501-1-094501-4, vol. 92, No. 9.

International Search Report for PCT/DK2013/050447 dated Mar. 21, 2014.

* cited by examiner

FLUID COMPOSITION ANALYSIS DEVICE AND METHOD

CROSS REFERENCE TO RELATED APPLICATIONS

This application is a U.S. National Phase Application of PCT International Application Number PCT/DK2013/050447, filed on Dec. 19, 2013, designating the United States of America and published in the English language, which is an International Application of and claims the benefit of priority to European Patent Application No. 12198606.1, filed on Dec. 20, 2012. The disclosures of the above-referenced applications are hereby expressly incorporated by reference in their entireties.

FIELD OF THE INVENTION

The present invention relates to a device and a method for the determining one or more flow properties of a fluid. The invention relates in particular to a device for determining one or more fluid properties of a fluid. The device preferably comprises a flow distributor comprising a cavity, an inlet to the cavity, one or more outlets from the cavity, and one or more flow deflecting elements present in the cavity and/or one or more flow dividing wall elements of the cavity, wherein the one or more flow deflecting elements and/or the flow dividing wall elements being arranged in such a manner that it provides sub-streams of different strength through the outlet. Furthermore, the device comprises an analyser downstream of the outlet of the flow distributor comprising means adapted to provide a read-out indicative of the strengths of sub-streams.

BACKGROUND OF THE INVENTION

Reference is made to WO 2009/061943 A9, Publication 14 May 2009 Entitled: Micro Rheometer for measuring flow viscosity and elasticity for micro sample volumes, and Helen L. Bandey et al. (Helen et al), Blood rheological characterization using the thickness-shear mode resonator, Biosensors and Bioelectronics 19, 1657 (2004).
Choice of Materials
The device described in WO 2009/061943 A9 involves electrodes of Au (gold), and it is therefore very sensitive to high temperatures. The devices disclosed in WO 2009/061943 A9 are explicitly described as being fabricated using clean-room techniques, which involve less corrosion and heat-resistive metals.
Mobility And Robustness Against Varying Working Conditions
Even though the fluid characterization in both WO 2009/061943 A9 and Helen et al involves small microchannel, these two devices, as described in WO 2009/061943 A9 and Helen et al., cannot be realized in a mobile handheld device of the same dimensions and weight as for the invention (described above), because they both depend on a pump producing a fixed precise volume-flowrate. With present prior art technology, such pumps must be syringe-pumps, which exceeds more than 10 fold the volume and weight of the invention, as described above.
Further Drawback
The devices and methods disclosed in WO 2009/061943 A9 and Helen et al also suffer the draw back of being less efficient, difficult to produce and sensitive to external influences.

OBJECT OF THE INVENTION

Hence, improved devices and methods for determining one or more properties of fluid would be advantageous, and in particular a more efficient and/or reliable device and method would be advantageous.

It is a further object of the present invention to provide an alternative to the prior art.

In particular, it may be seen as an object of the present invention to provide a device and a method that solves the above mentioned problems of the prior art.

It is a further object of the present invention to provide an alternative to the prior art.

SUMMARY OF THE INVENTION

Thus, the above described object and several other objects are intended to be obtained in a first aspect of the invention by providing a device for determining one or more fluid properties of a fluid. The device preferably comprises
i) a flow distributor comprising
   a cavity,
   an inlet to the cavity,
   one or more outlets from the cavity, and
   one or more flow deflecting elements present in the cavity and/or one or more flow dividing wall elements of the cavity, wherein the one or more flow deflecting elements and/or the flow dividing wall elements being arranged in such a manner that it provides sub-streams of different strength through the outlet,
ii) an analyser downstream of the outlet of the flow distributor comprising means adapted to provide a read-out indicative of the strengths of sub-streams.

Preferably, the flow distributor has two outlets and the one or more flow deflecting elements and/or the flow dividing wall elements being arranged in such a manner that they define at least two flow channels, said at least two flow channels have different lengths. Each of these channel preferably proceed from the inlet to an outlet with different variation in cross sections and/or in curvature at least along a part of the channel, thereby the flow channels being configured to divide a fluid flowing through inlet into separate substreams flowing out of a separate outlet with different strength.

Further, analyser is typically arranged immediate downstream of the outlets of the flow distributor and receives the fluid flowing out of the outlets.

A channel is preferably defined herein to be geometrical confined space, typically confined by wall elements at least along a part of the channel. Within that definition is considered a situation (as in FIG. 3) where the channel during at least a part of it extension is defined by a stream line. A channel is typically defined to extend from an inlet (which may be shared with another channel) and to an outlet. A channel's wall elements may provide openings along the extension of the channel allowing e.g. a often minor part of the fluid in the channel to flow out one the channel and into e.g. a neighbouring channel. Channel as used herein typically refer to a three dimensional structure, where, however, one of the dimensions typically the height is often constant throughout the extend of the channel. A channel as used herein is preferably considered to extend along a mean line or camber line preferably defined as a set of points having equal distance to the opposing channel walls/confinements, when measured along a direction perpendiculat to the flow direction A Cross section is typically defined as the cross section of a channel taken perpendicular to the mean line of the channel.

Curvature as used herein e.g. in the curvature of a channel is to be understood in broad terms and e.g. typically used to mean the value of the geometrical orientation of the tangent of the mean line.

Variation is used typically to mean changes in numerical value of the parameter considered.

The invention resides inter alia in the finding made by the inventor that feeding a fluid, in which the local dynamic viscosity depends on the local shear-rate of the fluid flow, through a flow distributor according to the present invention produces unique sub-streams of different strength. This can be disclosed e.g. by:

$$S_i(t)=F_i(W, Q_T(t), G, i)$$

where $S_i$ is the strength of the sub-stream i, W is the property of the fluid to be determined, $Q_T$ is the total volume flow into the cavity, G is the geometry of the cavity. Thus, by keeping $Q_T$ and G constant, the strength S of each sub-stream depends only the property W which can used to provide a correlation between S and W useable in the manner disclosed herein to determine the property W of a fluid. However, it is noted that the invention is also applicable in for $dQ_T(t)/dt$ being different from zero, although this often requires that the rate of change of the volume flow ($dQ_T(t)/dt$) is know and reproducible to allow for calibration and subsequently determining.

Due to the application of a total volume flow into the cavity, a pressure difference will (naturally) arise over the combined system of Distributor and Analyser, but this pressure does not convey any information used in determination of the property W of a fluid.

An advantage obtainable by the present invention is that pressure determinations may be avoided in relation to the present invention, as the outlet(s) may be arranged to deliver the outflow against the same pressure and as only one inlet is generally preferred.

It is generally preferred that the read-out indicative of the strengths of sub-streams is a common read-out in the sense that there is preferably not a single read-out for each sub-stream but typically a single read-out indicative of the strengths of the sub-streams.

It is noted that while many of the preferred embodiments is designed so that each sub-stream leaves the cavity through a separate outlet, the cavity may advantageously be designed to have only a single outlet. In the latter case, a sub-stream may be defined as the flow in a region where the flow strength has a local maxima.

The arrangement of the flow deflecting elements and/or the flow dividing elements is preferably made so as to provide flow paths inside the cavity, where the flow paths passes through constrictions, have different length, different curvature so as to produce a shear-rate sufficient to generate a local substantial change in dynamic viscosity that give rise to relative variations in the flow strength of the different sub-streams. It is noted that a flow paths may or may not be fully or partially restricted by solid elements.

The invention is particularly, but not exclusively, advantageous for obtaining a characterization of generalized Newtonian fluids, that is, fluids which local dynamic viscosity depends on the local shear-rate of the fluid flow, that is also denoted the shearing strain, which in a two dimensional form can be written as (having velocity components u, v in an coordinate system with axis x, y):

$$\dot{\gamma} = \sqrt{2\left(\frac{\partial u}{\partial x}\right)^2 + \left(\frac{\partial u}{\partial y} + \frac{\partial v}{\partial x}\right)^2 + 2\left(\frac{\partial v}{\partial y}\right)^2}$$

A number of terms used herein in a manner being ordinary for a skilled person will be elaborated further below.

Property is preferably used to means a characteristic of the fluid, such as concentration, composition, density, different value of dynamic viscosity depending on the local shear-rate, different value of kinematic viscosity depending on the local shear-rate, different value of shearing stress as a function of shear-rate The fluid may preferably be selected from the group consisting of visco-elastic fluids or the group consisting of thixotropic fluids. In preferred embodiments, the fluid is sugar dissolved in water and the property being determined is the sugar concentration, the fluid is paints and the property being determined is the rate of shear-thinning, the fluid is enamel and the property being determined is the rate of shear-thinning, the fluid is engine oil and the property being determined is the degradation of the oil, or the fluid is engine fuel and the property being determined is the type of engine fuel.

Cavity is preferably used to mean a void provided in or by a material being non-penetrable to the fluid. A cavity may preferably comprise a number of vertical wall sections and a horizontal top and bottom.

Inlet in relation with a cavity is preferably used to mean a channel leading or an opening into respectively out from a cavity.

Flow deflecting means is preferably used to means solid elements preferably being non-penetrable to the fluid and being arranged inside the cavity. Flow deflection means may preferably be embodied as one or more barriers inside the cavity of the flow distributor defines flow obstructions of different length and thickness, extending asymmetrically through the cavity as permeable barriers and confining a number of channels regions of different length, cross sectional area. The permeability of the barriers is typically provided by the barriers being separate elements arranged distanced from each other to provide openings between them. The flow preferably enters through the inlet into one of these channel regions, and it is typically during the passage of the fluid through one or more of the permeable barriers (into another channel region) that the fluid composition affects the relative flow strengths of the sub-streams.

Dividing wall elements is preferably used to mean at least part of the cavity walls. By dividing wall elements being arranged is preferably meant that the walls of the cavity is lay-out to obtain sub-streams of different strength.

Sub-stream is preferably used to mean a part of flow stream having a distinct local maxima of the flow strength. In embodiments where more than one outlet from the flow distributor is provided, each flow out of an outlet is preferably considered a sub-stream.

Flow strength is preferably used to mean the momentum of a flow. The flow strength is preferably determined as the square of the mean speed ($U^2$) of the flow considered.

Response is preferably used to mean a flow pattern inside the cavity.

Read-out is preferably used to mean an identifiable, visually, optically or electronically observable result.

Fluid is preferably used to mean a gas, or liquid or a mixture thereof.

In preferred embodiments, the one or more flow deflecting elements are barriers arranged inside the cavity.

A flow distributor according to preferred embodiments may preferably comprise a side wall, a top and a bottom defining box-shaped cavity and the inlet being provided in the side wall. In such embodiments, the barriers may advantageously be shaped as elongate elements with parallel sidewalls and extending from the top and to the bottom of the cavity.

In particular preferred embodiment, three barriers may be arranged inside the cavity. The barriers may advantageously being arranged downstream of each other and at different inclination relatively to the direction of the flow into the cavity at the inlet. Furthermore, the barriers may be distanced from each other providing opening in between them.

The flow distributor may preferably comprise a first outlet in the sidewall above and downstream of the most downstream arranged barrier and a second outlet in the sidewall below and downstream of the most downstream arranged barrier. Below and above refers preferably to an overall flow direction. Preferably, the cross sectional area of the first outlet is smaller than the cross sectional area of the second outlet.

The cavity may preferably comprise an upper and a lower side wall section and the barriers as well as the inlet may preferably be dislocated toward the upper side wall section.

In certain preferred embodiments, the cavity may comprise a bifurcation region and the flow dividing wall elements below and downstream of the bifurcation region provides a meander shaped channel leading to a first outlet of the cavity, and the flow diving wall elements upstream of the bifurcation region provides a diverging flow channel in the cavity. The flow dividing wall elements above the bifurcation region typically provides a second outlet of the cavity.

In preferred embodiments, the flow distributor may comprise an outlet for each sub-stream so that each sub-stream flows out of the cavity through a separate outlet.

The analyser may preferably comprise a flow channel connected via inlets to the one or more outlets of the flow distributor. The connection(s) may advantageously be direct in the sense that the fluid goes directly without flowing through further connections from the flow distributor to the analyser.

An analyser according to preferred embodiments may preferably comprise a separate flow channel for each outlet of the flow distributor, each separate flow channel being connected, preferably directly, to a separate outlet of the flow distributor.

The means adapted to provide a read-out indicative of the strengths of sub-streams may preferably comprises a moveable element, such as a bead, arranged in the channel(s) of the analyser. Such moveable element may advantageously be releasable arranged in the channel in a first position prior to feeding a not initial occupying fluid through the device.

In preferred embodiments, the means adapted to provide a read-out indicative of the strengths of sub-streams may comprise a gas bubble generator, arranged in the channel(s) of the analyser.

In further embodiments, the means adapted to provide a read-out indicative of the strengths of sub-streams may comprise fluid present in the channel(s) of the analyser.

In a second aspect, the invention relates to a method of determining one or more fluid properties by use of a device first aspect of the invention. The method preferably comprises feeding a pre-selected amount of fluid through the device,
observing the read-out indicative of the strengths of sub-streams, and
determining from the read-out the fluid property/properties based on a calibration containing corresponding values of fluid property/properties and read-outs Preferably, the step of feeding a pre-selected amount of fluid through the device is performed by feeding at constant volume flow the fluid into the device.

Alternatively, the step of feeding a pre-selected amount of fluid through the device is performed by feeding at non-constant volume flow the fluid into the device.

It is noted that feeding of a fluid through the device typically is the result of the fluid being fed through the inlet of the flow distributor.

The first, second aspect of the present invention may each be combined with any of the other aspects. These and other aspects of the invention will be apparent from and elucidated with reference to the embodiments described hereinafter.

BRIEF DESCRIPTION OF THE FIGURES

The present invention and in particular preferred embodiments thereof will now be described in more detail with regard to the accompanying figures. The FIGS. show ways of implementing the present invention and are not to be construed as being limiting to other possible embodiments falling within the scope of the attached claim set.

As noted herein, the results presented are obtained by Computational Fluid Dynamics as this approach provides details as to the flow which otherwise would be very difficult to obtain.

FIG. 2 shows a generalization of the concept of the divider in FIG. 1B, by allowing for more than two outlets, which increase the amount of information extracted from the device. Now the inlet flow rate is denoted $Q_T$, for the total flow rate; FIG. 2, flow distributor 1, which due to a complex geometrical channel-wall geometry (inside region G) deflects the sample fluid flow (entering though channel I) such that information about the composition of the fluid (solution concentration c) is reflected in the flow rates of the two or more outlets ($Q_1$, $Q_2$, $Q_3$ etc.).

DETAILED DESCRIPTION OF AN EMBODIMENT

Reference Numbers Used Herein

Figure 1:
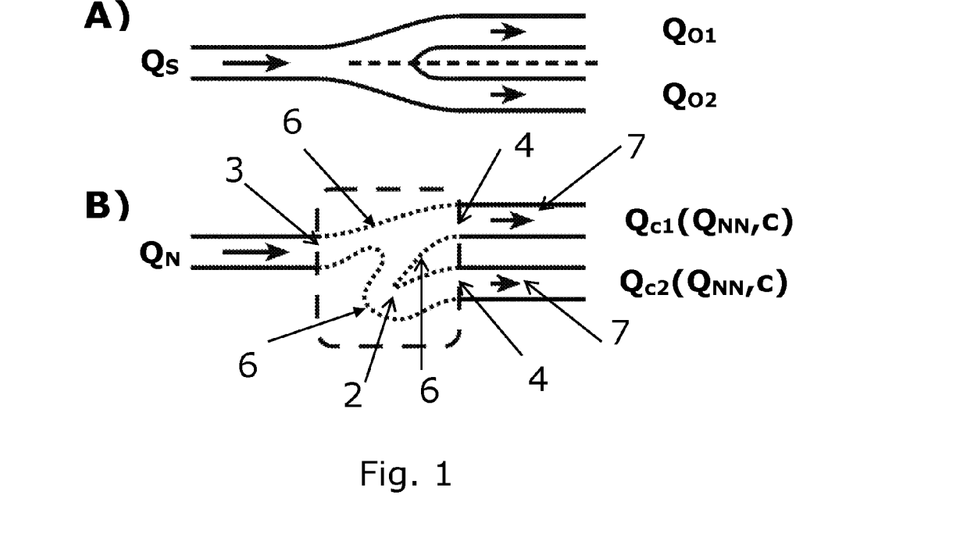
FIG. 1 is an illustration of the general concept behind the invention. Both for Newtonian and Non-Newtonian fluids, the division A) will split the flow rate in halves since the division is symmetric. Furthermore this property will be shear independent. On the contrary, the asymmetric complex geometry of division B) will give rise to non-linear difference between the two sub-flow rates $Qc_1$ and $Qc_2$, depending both on the overall flow rate and the fluid composition.

In the present context, various elements of devices according to the invention have been disclosed with reference to the accompanying drawings. In this referencing the following notation has been used:
1: flow distributor
2: cavity of the flow distributor 1
3: Inlet to the cavity 2
4: Outlet from the cavity 2
5: flow deflecting elements
6: flow dividing wall elements
7: sub-stream
8: Analyser
9: Bifurcation region
10: Inlet of analyser 8
11: Channel of analyser 8
12: Opening Core Concept of the Invention To illustrate the core concept, first draw the attention to simple Newtonian fluids (with no shear-dependence of the viscosity, such as pure water, and most gasses). In this case, imagine a channel that supports a flow rate $Q_S$ (passing volume pr. time) divides into two sub-channels further downstream, as shown in FIG. 1A. Then their respective flow rates $Q_{O1}$, and $Q_{O2}$, will sum up to $Q_S$ due to volume conservation, and be equal due to the symmetry of the channels $Q_{O1}=Q_{O2}$. Using Non-Newtonian fluids will also give equal flow rates, again due to symmetry.

A completely different response occurs, if the above procedure is repeated, but now by passing the fluids through a division, having a non-symmetric geometry, as shown in FIG. 1B. If the flow is kept flow laminar (e.g. let the corresponding Reynolds number be below one), the Newtonian fluids will give rise to unequal values of the flow rates ($Q_{C1} \neq Q_{C2}$) but their ratio ($Q_{C1}/Q_{C2}$) will remain the same, independent of the overall flow rate $Q_{NN}$, and the fluid composition (here represented by a solution concentration c). Passing Non-Newtonian fluids through, the flow rates, $Q_{C1}(Q_{NN},c)$, $Q_{C2}(Q_{NN},c)$, will now depend both on the overall flow rate $Q_{NN}$, and on the fluid composition c, and that is what is utilized in this invention.

The channel geometry of the asymmetric flow distributor 1 of FIG. 1B can then be structurally optimized to enhance especially the fluid response utilized in the specific embodiments of the invention. This structural optimization can be strongly aided by the use of e.g. topology optimization methods. A generalization of the divider in FIG. 1B will in the following be denoted the flow distributor.

Flow Distributor 1

Figure 2:
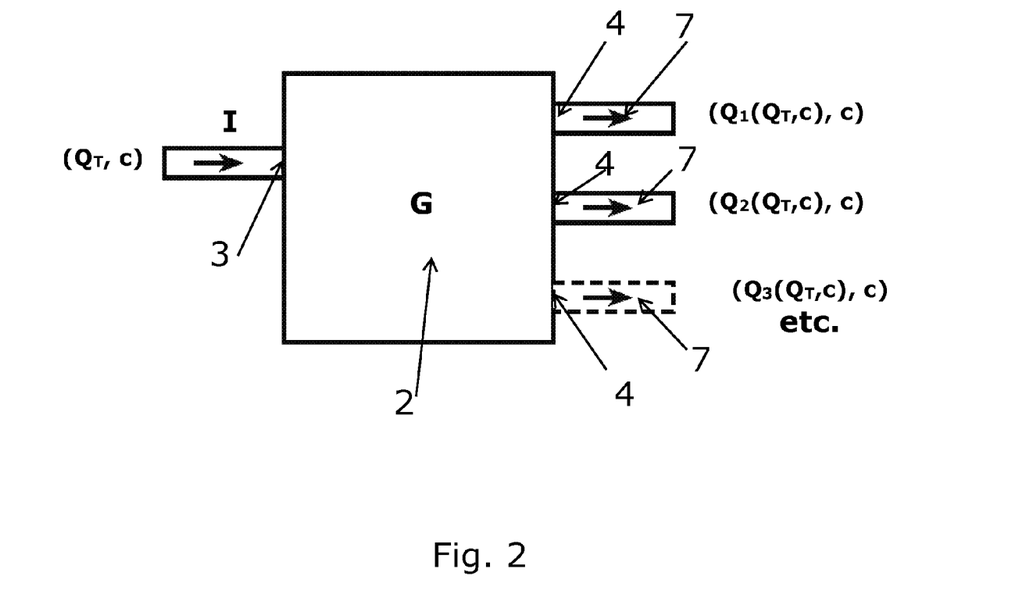

FIG. 2 generalizes the concept of the flow distributor in FIG. 1B, by allowing for more than two outlets, which increase the amount of information extracted from the devise. Now the inlet flow rate through inlet 3 is denoted $Q_T$, for the total flow rate.

In general terms, the flow distributor 1 will deflect the fluid flow, such that information about the fluid composition c can be extracted from the information coming from the following measurable quantities: $Q_T$, $Q_1$, $Q_2$, $Q_3$ etc. The flow $Q_1$, $Q_2$, $Q_3$ etc each leaves the flow distributor 2 through a separate outlet 4 and are each considered a sub-stream. This extraction of fluid composition information may be seen as a core part of the invention, and besides a first numerical modeling of the response from the flow distributor 1, the remaining description of the invention will include two different methods for easy extraction of the fluid composition information from the quantities: $Q_T$, $Q_1$, $Q_2$, $Q_3$ etc.

Numerical Modeling of the Flow Distributor 1

Figure 3:
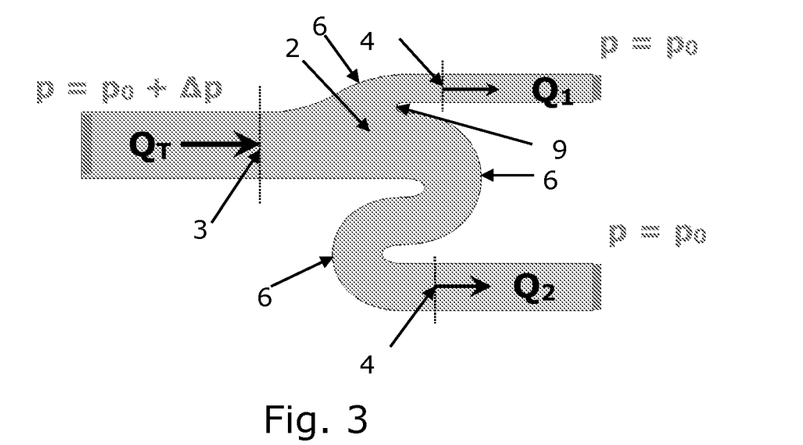
FIG. 3 shows a channel geometry of the numerical model of the flow distributor 1. Flow rates and inlet/outlet pressures are indicated in the model. The width of the inlet channel is 0.35 mm.

The channel geometry is shown in FIG. 3, where the width of the inlet channel is 0.35 mm, and flow rates are defined together with the driving pressure difference on the inlet/outlets.

As shown in FIG. 3, the wherein cavity 2 comprises a bifurcation region 9 and the flow dividing wall elements 6 below and downstream of the bifurcation region 9 provides a meander shaped channel leading to a first outlet 4 of the cavity 2. The flow diving wall elements 6 upstream of the bifurcation region 9 provides a diverging flow channel in the cavity, and the flow dividing wall elements 6 above the bifurcation region 9 provides a second outlet 4 of the cavity 2.

As shown in FIG. 3, the channel geometry defines at two flow channels with different lengths (the flow channels each onset at the inlet 3 and proceed to the one of the outlets 4). In the embodiment of the distributor of FIG. 3, the division of the void into two channel (upper and lower channel) is typically defined to be the stagnation streamline ending at the point of bifurcation on 9 (see e.g. FIG. 7 for an examples on streamlines). Furthermore, they each proceeds from the inlet 3 to an outlet 4 with different variation in cross sections and in curvature at least along a part of the channel (in the passages close to the outlet, the variation in cross sections and curvature is zero).

While the results presented herein is obtainable in a pure experimental set-up, it is preferred to present results based on numerical simulation as this provide an easier insight in the flow phenomena obtained.

The modeled fluid is based on mimicking the flow response of blood, and while this "blood" is denoted "fluid1", two other fluids are tested: A diluted version of blood (fluid2), and another Non-Newtonian fluid (fluid3). All fluids are modeled using the Carreau-Yasuda model:

$$\eta(\dot{\gamma}) = \eta_{2s} + (\eta_0 - \eta_\infty)[1 + (\lambda\dot{\gamma})^\alpha]^{(n-1)/\alpha},$$

where $\dot{\gamma}$ is the local shear-rate of the fluid, and the remaining quantities for the three fluids are given in the following Table 1

TABLE 1

The related quantities for the three Carreau-Yasuda fluids

| Quantity | $\eta\infty$ (Pa * s) | $\eta 0$ (Pa * s) | $\lambda$ (s) | a (1) | n (1) |
|---|---|---|---|---|---|
| Fluid1 | 70 | $10^{-2}$ | 100 | 2 | 0.15 |
| Fluid2 | 10 | $10^{-2}$ | 50 | 2 | 0.25 |
| Fluid3 | 40 | $10^{-1}$ | 100 | 2 | 0.4 |

Figure 4:
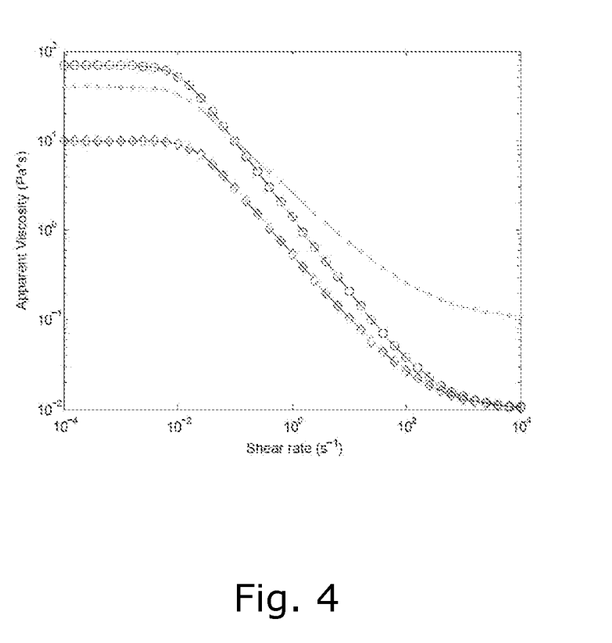
FIG. 4 shows the shear dependence of the viscosity for the three fluids, where circles are fluid1, rhombs are fluid2, and dots are fluid3.
Figure 5:
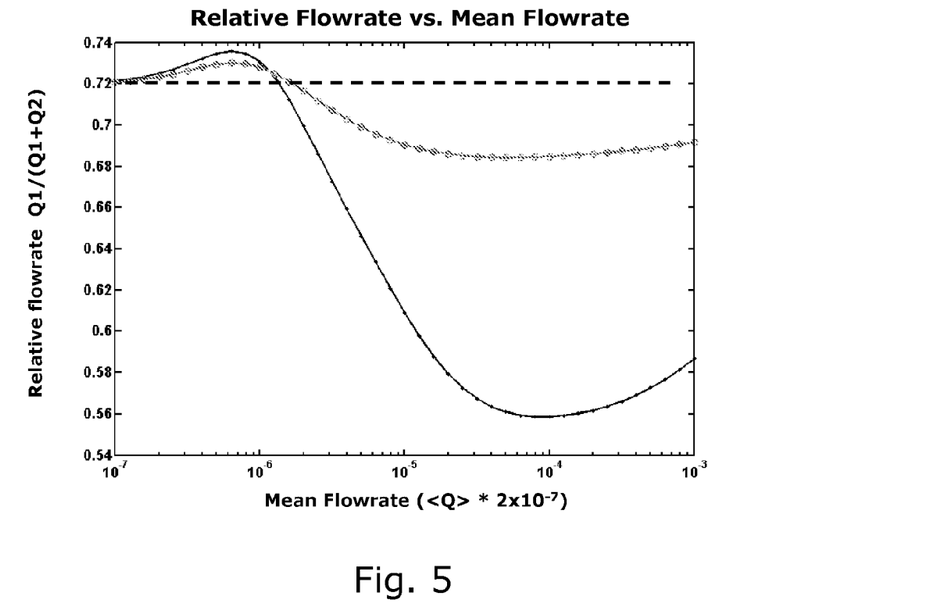
FIG. 5 shows the relative flow rates $Q_1/(Q_1+Q_2)$ as a function of the mean flow rate $(Q_1+Q_2)/2$ obtained by the flow distributor shown in FIG. 11 and for two different fluids.

A graphical representation of the shear-depending viscosity for the three fluids is shown in FIG. 4.

Now for each given value of the pressure difference $\Delta p$ (see FIG. 3) in the range 1-1000 Pa, the numerical model is solved using the commercial simulation tool COMSOL or by any other ordinary numerical simulation tool, capable of solving the Navier-Stokes equations with the prescribed Carreau-Yasuda model of a shear-dependent viscosity, and the two outlet flow rates $Q_1$, $Q_2$ are measured.

Figure 6:
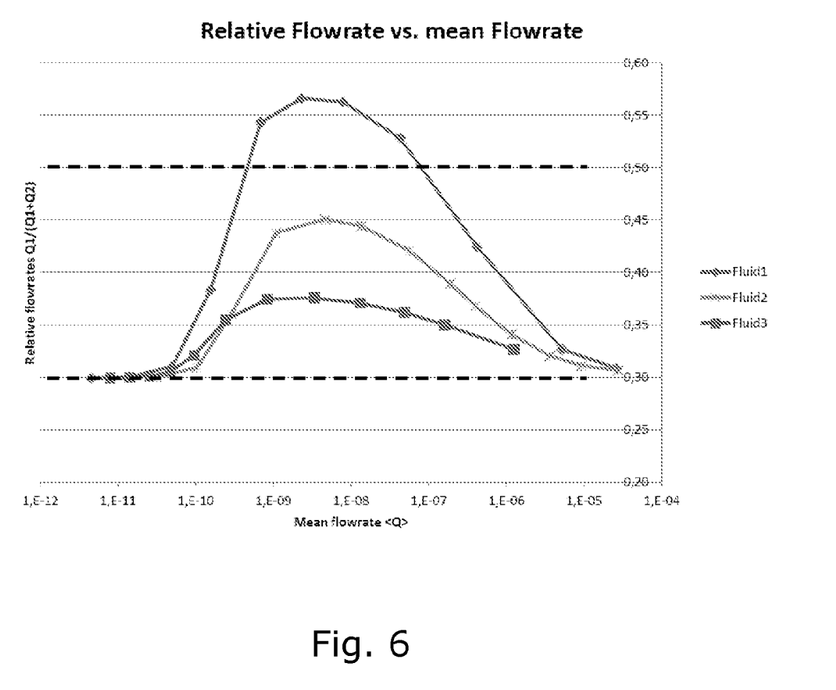
FIG. 6 shows the relative flow rates $Q_1/(Q_1+Q_2)$ as a function of the mean flow rate $(Q_1+Q_2)/2$ and for the three different fluids obtained with the flow distributor shown in FIG. 3. The lower dotted line corresponds to the relative flow rates coming from a Newtonian flow, and the upper dashed line shows the value ½, above which $Q_1>Q_2$ and below which $Q_2>Q_1$.

To better investigate the flow response as a function of different overall flow rates and types of fluids, FIG. 6 shows the relative flow rates Q1/(Q1+Q2) as a function of the mean flow rate (Q1+Q2)/2 and for the three different fluids.

As the response from a Newtonian fluid would be independent of the overall flow rate, the corresponding curve for a Newtonian fluid in FIG. 6 would be the lower dotted black line, where the constant relative flow rate simply is determined by the difference in the hydraulic resistance between the two channels after the division.

Then when the fluids introduce non-linear internal responses, the corresponding curves will exhibit deviations from the constant dotted line, and that is exactly what is seen by the response curves from the three Non-Newtonian fluids in FIG. 6, where the deviation happens for intermediate values of the shear. It is clear from the response curves in FIG. 6 that the magnitude of the deviation varies between the three fluids but also features like the distinct positions of the maxima etc. yield information about the given fluid composition, which all in all can be used in the case of evaluating the fluid composition of a given unknown fluid sample.

Figure 7:
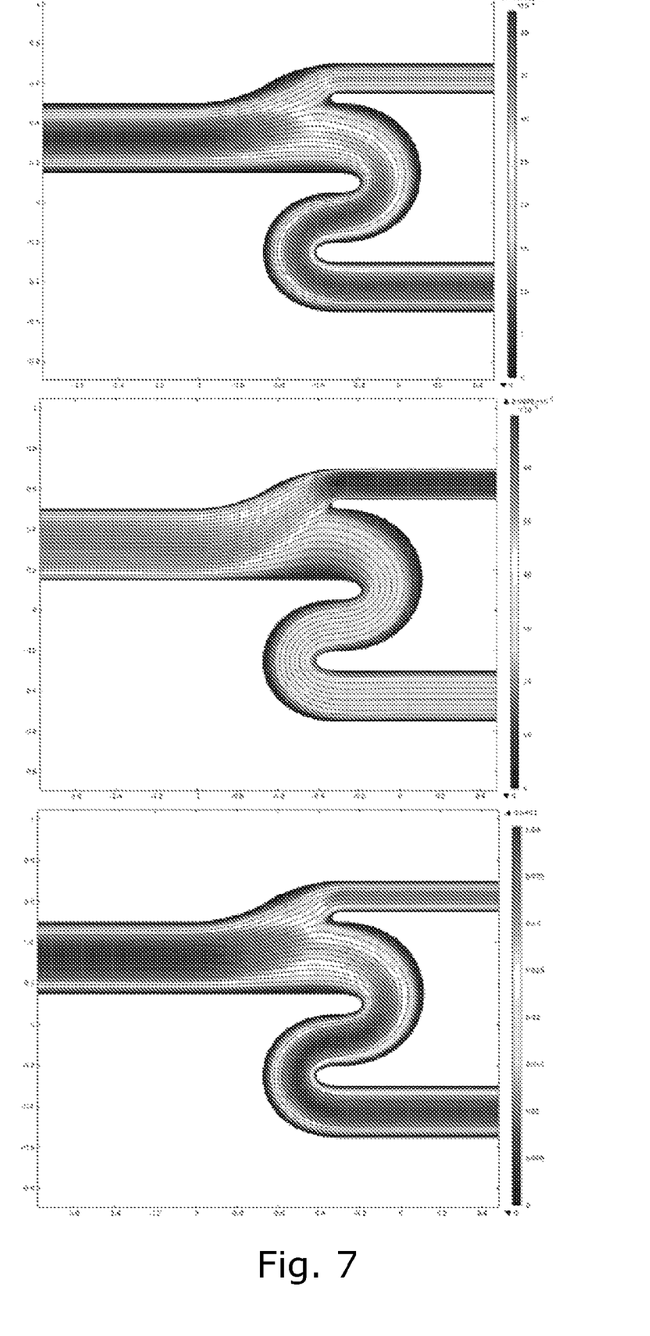
FIG. 7 shows the resulting flow patterns in the fluid distributor 1 (fluid1) for different driving pressures. The flow-pattern is showed by black stream-lines, and the flow speed is illustrated using gray-shading-coding (darker means higher flow speed). Upper most figure ΔP=10 Pa; middle figure ΔP=45 Pa and lower most figure ΔP=300 Pa.

The resulting flow patterns of the flow distributor 1 (fluid 1) for different driving pressures are shown in FIG. 7.

Analysis Parts in Connection to the Flow Distributor 1

As disclosed herein, an analyser 8 is provided downstream of the outlet/outlets of the flow distributor 1. The analyser 8 comprises means adapted to provide a read-out indicative of the strengths of sub-streams. Further details as to these means are presented below, with reference to some overall concepts of the analyser 8.

A purpose of the analyser is to provide a read-out correlated to magnitude of property to be determined, and the magnitude of the property is correlated with the strength of the sub-streams. The strength of the sub-streams may be seen fluid dynamically to be momentum which can be used to transport either elements contained in the fluid.

The strength of the sub-streams may vary in time. However, according to an overall concept of the invention, by keeping a total volume flow applied through the inlet fixed, and applying this total volume flow with a well-known and reproducible history of total flow strength in time, for instance a bead flowing with the sub-streams will end at a characteristic position depending on the fluid composition. One possible embodiment of an analyser, using this principle is the Analyser 8 illustrated in FIG. 8.

By "keeping a total volume flow applied through the inlet fixed" is typically meant that the amount of fluid flowing through the inlet is the same from one determination of a fluid property to the next determination and is furthermore the same as was used during calibration of the device Another concept of the invention, in the case where the total volume flow applied through the inlet is not fixed, and the total volume flow is applied without a well-known and reproducible history of total flow strength in time, is to measure in time the history of flow strengths of the sub-streams. The strength of the sub-streams may be at least indicated by detecting the transportation carried by the sub-streams. By knowing the time-history of flow strengths of the sub-streams, the fluid composition can be deduced from the information of the response-curves of the applied flow distributor (see e.g. FIG. 6). One possible embodiment of an analyser, using this principle is the "Analyser 8" illustrated in FIG. 10.

A practical implementation for applying volume flow through the inlet may be in the form of a plunger mechanism, such as a dosing pump or a syringe. Such a plunger mechanism may be mechanically activated to produce a volume flow through the inlet being well defined both in time as well as the total amount. In case of a manually activated syringe e.g. the total amount may be fixed but the time resolution may be undefined. In this case, the property is determined by determining the resulting time-dependent read-out.

Suitable means for detecting the strength of the sub-streams includes:
- beads
- gas bubbles produced e.g. by a platinum wire with voltage
- interface/transition between two fluid Such means has the further advantages that they makes it possible
- to measure and/or visualize the sub-streams flow rate history through the n-outlet from fluid divider
- timely decompose the strength of the sub-streams independently of the inflow pattern or history
- time integrating the strength, as the flow rate integration sums to total inflow.

Accordingly, an analyser 8 (see e.g. FIG. 8) may preferably comprise a flow channel 11 connected via inlets 10 to the one or more outlets 4 of the flow distributor 1. Alternatively, the analyser 8 (see e.g. FIG. 11) may comprise a separate flow channel 11 for each outlet 4 of the flow distributor 1 where each separate flow channel 11 is connected to a separate outlet 4 of the flow distributor 1.

Figure 8:
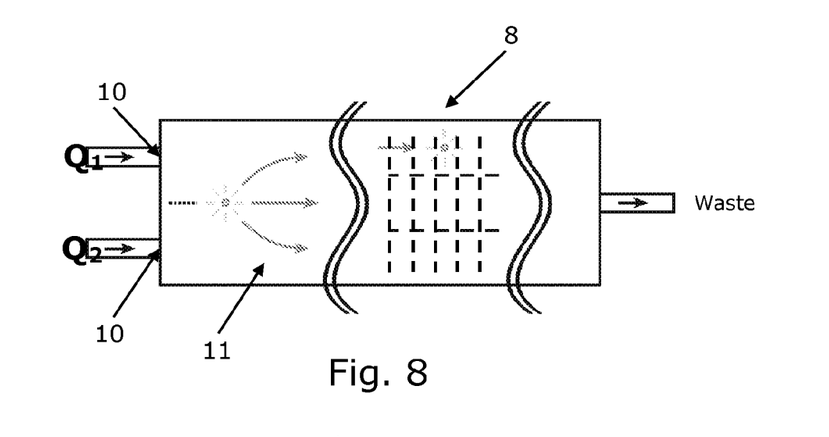
FIG. 8 is an illustration of an embodiment of an analyser 8 (termed Analyser 8 herein) for easy information extraction. Depending on the relative flow rates of the inlets, Q1 and Q2, the "brightly colored" bead (shown as a star in FIG. 8) will be convected downstream along different flow paths from its initial position as illustrated by the three arrows originating from the bead's original position in the analyser. Once the finite sample has been injected through the device for determining one or more fluid properties, the flow stops, and the reading of the final position of the bead can be done directly, using the tick-marks on the transparent upper wall of the analyser 8, which can be related to the composition of the fluid, being analyzed by the device.

The means adapted to provide a read-out indicative of the strengths of sub-streams may preferably comprise a moveable element, such as a bead, arranged in the channel(s) of the analyser (see FIG. 8). Moveable means that it is moved by and along with the fluid. The moveable element is typically provided from a material having a density similar to density of the fluid to avoid buoyancy related problems (to light density) or inertia related problems (to high density).

The moveable element is typically releasable arranged in the channel in a first position prior to feeding a fluid through the device, so as to be able to be able to determine the movement of the element relatively to a known (first) position. The reliable arrangement may be provided by the element being attached to the surface of the channel by a dissolvable substance, by a weak magnetic force and arranged in an indentation.

Alternatively, the means adapted to provide a read-out indicative of the strengths of sub-streams may comprise a gas bubble generator, arranged in the channel(s) of the analyser.

Further alternatives for the means adapted to provide a read-out indicative of the strengths of sub-streams may comprise a fluid present in the channel(s) of the analyser. This fluid may be immiscible with the fluid already present in the flow distributor, and the fluid fed into the device 1 in which case the interface between the two fluid moves downstream in the channel(s) of the analyser, or the fluid may be miscible and e.g. colored where by the mixing will result in a change in color.

Now follows descriptions of two examples on devices and methods for easy extraction of the fluid composition information from the set of flow rates $Q_1$, $Q_2$, $Q_3$ etc. supplied by the flow distributor 1. These analysis parts should then be placed in direct continuation of the flow distributor 1.

Analog Analyser 8 for Easy Information Extraction

In order to aid the development of the invention into a simple disposable "Single-step Fluid Composition Analysis microchip", the following analyser 8 has been devised, which functions purely due to fluid convection, with no dependence on external electronic or digital processing. This disposable sub-unit is capable of making a single fluid characterization, and may be manufactured directly as a single piece of in transparent polymer of estimated possible size 80×40×3 mm. It depends on the convection of a "brightly colored" small bead by the combined flows, driven by the outlets from the flow distributor 1, and is illustrated in FIG. 8.

As shown in FIG. 8, the analyser 8 comprises inter alia a flow channel 11 connected via inlets 10 to the one or more outlets 4 of the flow distributor 1.

The functionality of the analyser 8 is as follows: Depending on the relative flow rates through the inlets 10, Q1 and Q2, the "brightly colored" bead (the "star" in FIG. 8) will be convected downstream along different flow paths from its initial position, as illustrated by the three arrows originating from the bead's initiation position. Once a finite sample has been injected through the device for determining one or more fluid properties (consisting of the flow distributor 1 in direct fluidic connection to the analyser 8), the flow stops, and the final position of the bead can be read off directly, using the tick-marks on the transparent upper part of the analyser 8. The position then directly relates to the composition of the fluid which has to be analyzed by the device.

In the present embodiment of the invention, the device for determining one or more fluid properties has to be filled with a transparent buffer fluid prior to the injection of the sample in order to avoid formation of internal non-miscible fluid/gas- and fluid/fluid-interfaces, which will strongly alter the response from given by the device.

Digital Analyser 8 for Easy Information Extraction

When a more precise numeric value is required for characterizing the given composition of the fluid, the following "Digital Analysis-setup" can be applied, which consists of the combination of one simple disposable sub-unit (cartridge) of estimated possible size 20×50×2 mm, and one non-disposable measuring-station of estimated possible size 100×70×40 mm, which measures the different flow rates using build-in optical detection system, and converts it into the requested quantity, either being presented on an integrated display for mobile use, or transmitted to an external computer for analysis/storage.

The cartridge consists of both the flow distributor 1 with fluid-connection to a sub-unit for optical detection. Thereby the cartridge contains all the microfluidic channels, and may also be manufactured directly as a single piece of in transparent polymer. Both the cartridge and the measuring-station are schematically illustrated in FIG. 9.

An easy way to convert a flow rate into an optically measurable signal is to let the fluid flow gradually block the light path coming from a constant light-source, and converting the measured temporal attenuation of the transmitted light into the requested quantity using either the onboard processing unit or an external computer. This is done by two or more optical detection systems in the measuring-station, in order to get enough information about the fluid composition.

Figure 9:
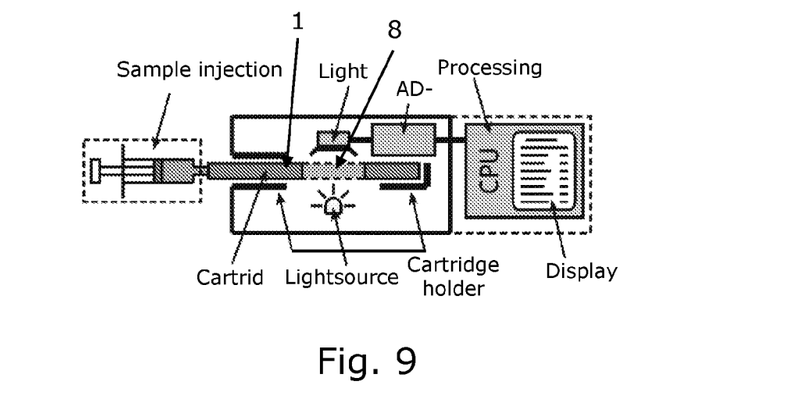
FIG. 9 shows schematically a cartridge, sample injection, and a measuring station. The cartridge is only used once for characterizing one sample fluid, after which it is disposed. In the illustration only one optical detection system is shown, while the following example of the cartridge sub-unit needs two independent detection systems.
Figure 10:
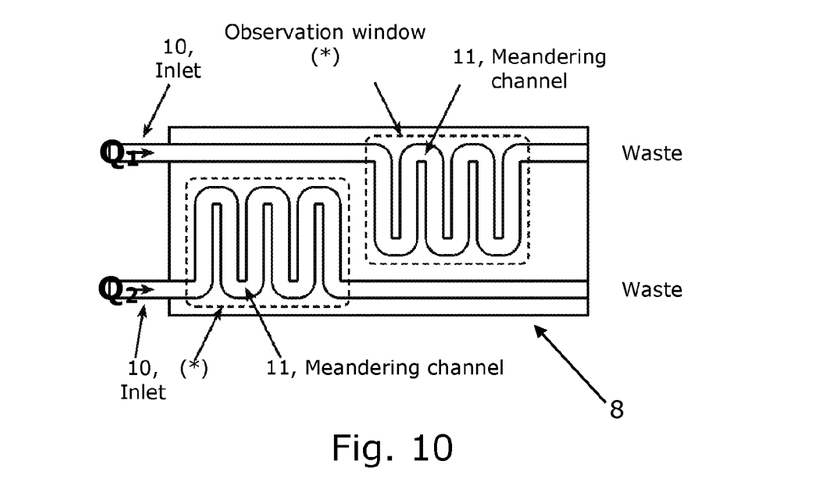
FIG. 10 shows schematically an analyser 8 to be used in connection with the flow distributor 1 to make up the disposable Cartridge for the Digital Analysis-setup. When the sample fluid fills up the meandering channels 11, the light intensity transmitted through the observation windows varies in time, and this temporal variation can be converted into information about the sample fluid composition.

FIG. 9 only shows one detection system to simplify the illustration. A schematic illustration of a possible sub-unit layout is shown in FIG. 10, where the gradual filling of the meandering channels 10 will attenuate the transmitted light, passing through the observation windows of the cartridge. If the fluid sample is not opaque, then the cartridge can be pre-filled with opaque buffer liquid, and the increase in light transmission can be measured instead.

Further Embodiments

Figure 11:
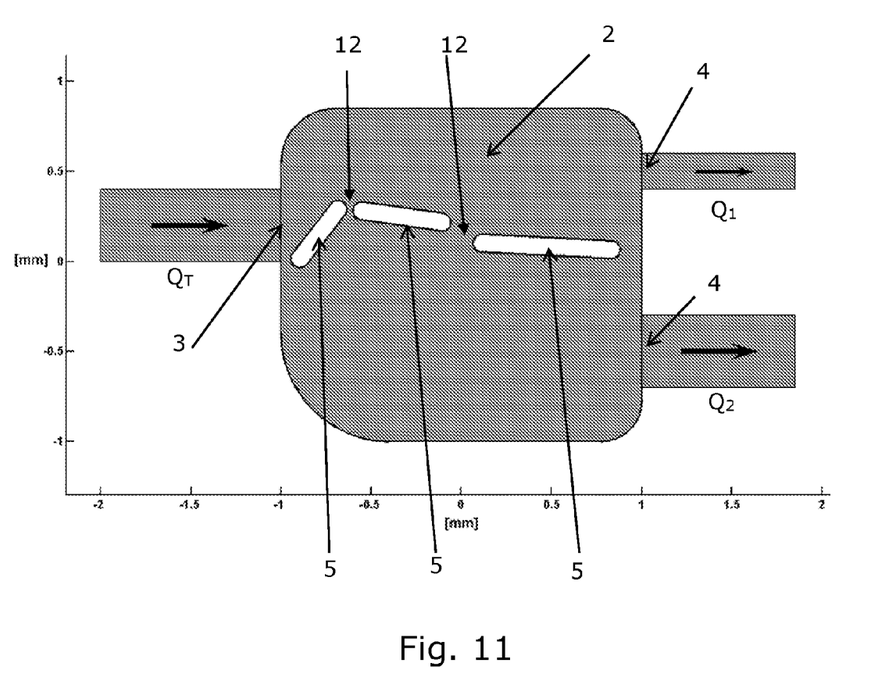
FIG. 11 shows schematically a flow distributor comprising a cavity with barriers (flow dividing elements) arranged inside the cavity and having two outlets.

A further embodiment of a fluid distributor 1 is disclosed schematically in FIG. 11. The fluid distributor 1, comprising comprises a side wall, a top and a bottom defining box-shaped cavity with rounded corners. The inlet 3 being provided in the side wall and the barriers 5 (flow deflecting elements) are shaped as elongate elements with parallel sidewalls and extending from the top and to the bottom of the cavity 2. The barriers 5 are as shown in the figure arranged distanced from each other providing openings 12 in between them.

In the embodiment of FIG. 11, three barriers 5 are arranged inside the cavity 2 although the invention is not limited to that number of barriers. The barriers 5 are being arranged downstream of each other and at different inclination relatively to the direction of the flow into the cavity 2 at the inlet 3.

The flow distributor 1 comprises a first outlet 4 in the sidewall above and downstream of the most downstream arranged barrier 5, and a second outlet 4 in the sidewall below and downstream of the most downstream arranged barrier 5. The cross sectional area of the first outlet 4 is smaller than the cross sectional area of the second outlet 4.

As shown in FIG. 11, the cavity 2 comprising an upper and a lower side wall section (extending from inlet 3 to an upper respectively lower outlet 4) and the barriers 5 and the inlet 3 is dislocated toward the upper side wall section.

Figure 12:
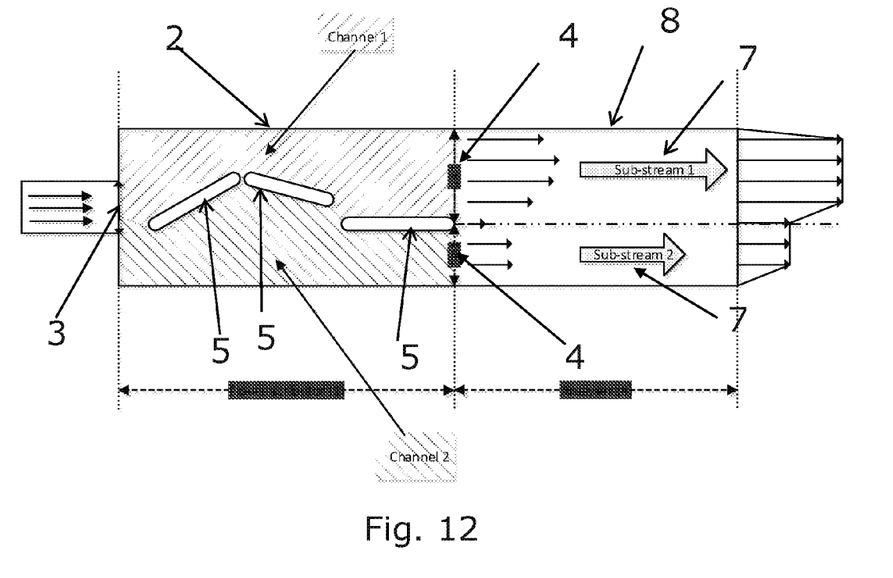
FIG. 12 shows schematically a device for determining one or more fluid properties in which the fluid distributor and analyser are built together and the flow distributor comprises only a single outlets being identical with the inlet of the analyser (hatchings denotes channel 1 and channel 2 respectively as indicated in the legend of FIG. 12).
Figure 13A:
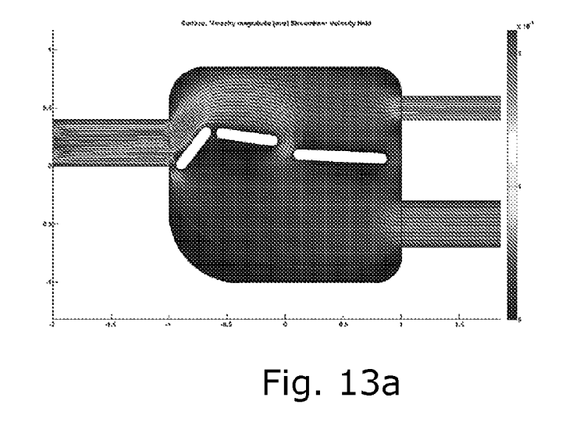
FIGS. 13a,b and c show flow patterns in the flow distributor disclosed in FIG. 11, the flow patterns are shown for three different mean flow-rates (with a overall channel height of 1 mm) a)=2×10$^{-11}$ m$^3$/s, b)=2×10$^{-13}$ m$^3$/s and c)=2×10$^{-14}$ m$^3$/s. It is preferred in many of the embodiments that the heights of the channels in the device are equal throughout the device and larger than lengths in of the channel so that a 2 dimensional flow situation is provided.
Figure 13B:
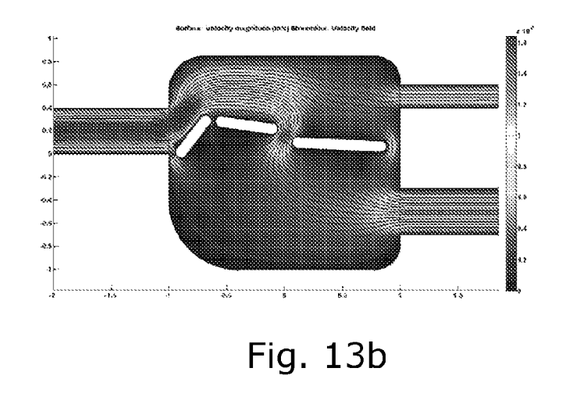
Figure 13C:
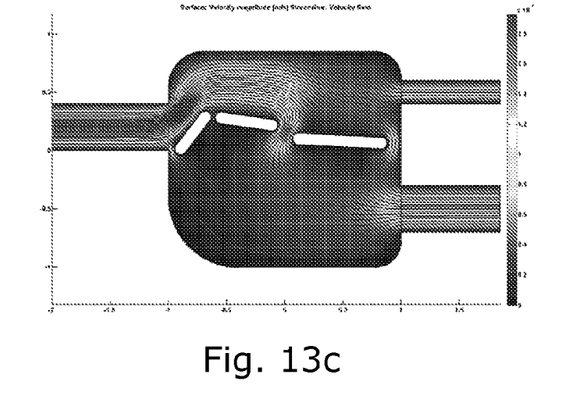

Depending on where the transition between the distributor 1 and the analyser 8 is said to be (and thereby the division between analyser and distributor), the flow distributor may be seen as having only a single outlet through which two sub-stream with different strengths flow. It is generally preferred to place the transition as indicated in FIG. 12, whereby two outlets 4 are present. However, if the transition is moved downstream the distributor 8 may be sees as having only a single outlet.

In addition, it is preferred that analyser 8 is arranged immediately downstream of the distributor 1, which typically means that the fluid flowing out of the distributor enters the analyser 8 without a change in momentum relatively to flow out of the distributor. Thus, in FIG. 12 e.g. the transition is cross section with zero thickness (as measured in the flow direction).

FIG. 12 shows further an example of a flow distributor 2 providing sub-streams 7 of different strength having separate outlets 4 for each sub-stream 7. The velocity profile out of the flow distributor 2 is sketched schematically slightly downstream of the outlets 4 by horizontal arrows (similarly to the way the velocity profile out of the analyser 8 is sketched).

As it appears from the sketched velocity profile at the outlets 4, this velocity profiled has a local minimum downstream of the most downstream flow deflecting element 5. This may be used to define a division of the flow into two sub-stream of different strength; the division is schematically shown as a dotted line above which sub-stream 1 is found and below which sub-stream 2 is found.

The strength of each of the subs-streams may be determined as $U^2$ where U is found by Q/A Q is the total flow rate above (respectively below) the division and A is the cross sectional area above (respectively below) the division or A is the cross sectional area of each outlet 4.

As shown in FIGS. 11 and 12, the channel geometry of the distributor defines at two flow channels with different lengths (the flow channels each onset at the inlet 3 and proceed to the one of the outlets 4). Furthermore, they each proceeds from the inlet 3 to an outlet 4 with different variation in cross sections and in curvature at least along a part of the channel.

Method of Use of the Analysis Device

Use of an analysis device 1 according to the present invention will in many instances be based on a calibration of the analysis device 1.

The calibration is carried out by feeding a fluid with different fluid compositions through the analysis device and recording the read-out of the analysis device. Considering as an example a situation, where the analysis device is to be calibrated to determine the concentration c of a liquid, say sugar concentration in blood, a number of calibration runs are carried.

Each calibration runs includes feeding a certain amount of the blood with a known sugar concentration through an analysis device 1 and recording the read-out R after the total amount has been fed into the analysis device 1.

When the read-out R is recorded, the device 1 is reset or a new identical device 1 is applied for carrying out the exact same calibration run.

This results in corresponding values of property, C, and read-out R:

| $C_1$ | $C_2$ | $C_3$ | $C_4$ | $C_4$ | $C_5$ | $C_6$ |
|---|---|---|---|---|---|---|
| $R_1$ | $R_2$ | $R_3$ | $R_4$ | $R_4$ | $R_5$ | $R_6$ |

The number of calibrations runs is shown to be six, however the actual number may be selected in accordance with a desired accuracy. The total volume flow $Q_T$ through the device for each calibration run should be kept constant; furthermore, as noted herein the timely variations in Q fed to the inlet of the device 1 has to be similar and reproducible in all the calibrations runs in order for the fluid composition to uniquely determine the final read-out R.

The read-out R may be the position of the bead in the embodiment of the analyser 8 shown in FIG. 8, the color of the liquid in the meandering channels 11 of the embodiment shown in FIG. 10 or any of the other read-out obtained by the analyser 8.

During use, this calibration is used to extract the property say the sugar concentration. As one of the sets of corresponding values of C and R of the above table is seldomly obtained during determination, an ordinary interpolation based on the closest or surrounding values of R is carried out to obtain a determined C.

Infeed of the fluid to the analysis device may advantageously be performed by a plunger mechanism e.g. a syringe as disclosed in FIG. 9 labelled sample injection.

Although the present invention has been described in connection with the specified embodiments, it should not be construed as being in any way limited to the presented examples. The scope of the present invention is set out by the accompanying claim set. In the context of the claims, the terms "comprising" or "comprises" do not exclude other possible elements or steps. Also, the mentioning of references such as "a" or "an" etc. should not be construed as excluding a plurality. The use of reference signs in the claims with respect to elements indicated in the figures shall also not be construed as limiting the scope of the invention. Furthermore, individual features mentioned in different claims, may possibly be advantageously combined, and the mentioning of these features in different claims does not exclude that a combination of features is not possible and advantageous.

The invention claimed is:

1. A device for determining one or more fluid properties of a fluid, the device comprising:
   i) a flow distributor comprising:
      a cavity having an inlet and at least two outlets
      one or more flow deflecting elements present in the cavity and/or one or more flow dividing wall elements of the cavity,
      wherein the one or more flow deflecting elements and/or the flow dividing wall elements are arranged such that they define at least two flow channels, said at least two flow channels having different lengths, each proceeding from said inlet to an outlet with different variation in cross sections and in curvature at least along a part of the channel, thereby the flow channels being configured to divide a fluid flowing through said inlet into separate substreams flowing out of a separate outlet with different strength; and
   ii) an analyser arranged downstream, of the outlets of the flow distributor and receiving the fluid flowing out of the outlets, the analyser comprising a read-out indicative of the strengths of sub-streams.

2. The device according to claim 1, wherein the one or more flow deflecting elements are barriers arranged inside the cavity.

3. The device according to claim 2, wherein the flow distributor comprises a side wall, a top and a bottom defining a box-shaped cavity and the inlet being provided in the side wall; and wherein the barriers are shaped as elongate elements with parallel sidewalls and extending from the top and to the bottom of the cavity.

4. The device according to claim 3, wherein three barriers are arranged inside the cavity, the barriers being arranged downstream of each other and at different inclination relative to the direction of the flow into the cavity at the inlet.

5. The device according to claim 3, wherein the flow distributor comprises a first outlet in the sidewall above and downstream of the most downstream arranged barrier, and a second outlet in the sidewall below and downstream of the most downstream arranged barrier.

6. The device according to claim 5, wherein the cross sectional area of the first outlet is smaller than the cross sectional area of the second outlet.

7. The device according to claim 3, wherein the cavity comprises an upper and a lower side wall section and, wherein the barriers and the inlet are dislocated toward the upper side wall section.

8. The device according to claim 1, wherein the cavity comprises a bifurcation region and, wherein:
the flow dividing wall elements below and downstream of the bifurcation region provide a meander shaped channel leading to a first outlet of the cavity, and
the flow dividing wall elements upstream of the bifurcation region provide a diverging flow channel in the cavity, and
the flow dividing wall elements above the bifurcation region provide a second outlet of the cavity.

9. The device according to claim 1, wherein the analyser comprises:
a flow channel connected via inlets to the one or more outlets of the flow distributor.

10. The device according to claim 9, wherein the read-out indicative of the strengths of sub-streams comprises a moveable element or a bead, arranged in the channel(s) of the analyser.

11. The device according to claim 10, wherein the moveable element is releasably arranged in the channel in a first position prior to feeding a not initial occupying fluid through the device.

12. The device according to claim 9, wherein the read-out indicative of the strengths of sub-streams comprises a gas bubble generator, arranged in the channel(s) of the analyser.

13. The device according to claim 9, wherein the read-out indicative of the strengths of sub-streams comprises a fluid present in the channel(s) of the analyser.

14. The device according to claim 1, wherein the analyser comprises a separate flow channel for each outlet of the flow distributor, each separate flow channel being connected to a separate outlet of the flow distributor.

15. A method of determining one or more fluid properties by use of a device according to claim 1, the method comprising:
feeding a pre-selected amount of fluid through the device of claim 1,
observing the read-out indicative of the strengths of sub-streams, and
determining from the read-out the fluid property/properties based on a calibration containing corresponding values of fluid property/properties and read-outs.

16. The method of determining one or more fluid properties according to claim 15, wherein the feeding of a pre-selected amount of fluid through the device is performed by feeding the fluid into the device at a constant volume flow.

17. The method of determining one or more fluid properties according to claim 15, wherein the feeding of a pre-selected amount of fluid through the device is performed by feeding the fluid into the device at non-constant volume flow.

* * * * *